US007625336B2

(12) United States Patent
Fukuyama et al.

(10) Patent No.: US 7,625,336 B2
(45) Date of Patent: Dec. 1, 2009

(54) ELECTRONIC ENDOSCOPE SYSTEM WITH FUNCTIONALLY ALTERABLE OPERABLE MEMBERS

(75) Inventors: Mitsufumi Fukuyama, Saitama-ken (JP); Hideo Sugimoto, Tokyo (JP)

(73) Assignee: Hoya Corporation, Tokyo (JP)

( * ) Notice: Subject to any disclaimer, the term of this patent is extended or adjusted under 35 U.S.C. 154(b) by 908 days.

(21) Appl. No.: 11/275,418

(22) Filed: Dec. 30, 2005

(65) Prior Publication Data

US 2006/0173240 A1 Aug. 3, 2006

(30) Foreign Application Priority Data

Jan. 5, 2005 (JP) ............................. 2005-000948

(51) Int. Cl.
*A61B 1/04* (2006.01)
*A61B 1/06* (2006.01)

(52) U.S. Cl. ...................... 600/118; 600/103; 600/160; 600/131

(58) Field of Classification Search ................. 600/103, 600/131, 118, 117, 160; 348/74
See application file for complete search history.

(56) References Cited

U.S. PATENT DOCUMENTS

| 4,979,497 | A | | 12/1990 | Matsura et al. |
| 5,050,584 | A | | 9/1991 | Matsuura |
| 5,609,563 | A | | 3/1997 | Suzuki et al. |
| 5,894,322 | A | * | 4/1999 | Hamano et al. ............... 348/68 |
| 6,120,435 | A | * | 9/2000 | Eino ............................ 600/118 |
| 6,602,186 | B1 | * | 8/2003 | Sugimoto et al. ........... 600/126 |
| 6,635,011 | B1 | * | 10/2003 | Ozawa et al. ............... 600/178 |

(Continued)

FOREIGN PATENT DOCUMENTS

JP 6-054794 3/1994

(Continued)

OTHER PUBLICATIONS

English Language Abstract of JP 6-054794, (Mar. 1994).

(Continued)

*Primary Examiner*—John P Leubecker
(74) *Attorney, Agent, or Firm*—Greenblum & Bernstein P.L.C.

(57) ABSTRACT

An electronic endoscope system for observing living tissues inside a body cavity includes an illuminating apparatus having a white light source emitting white light and an excitation light source emitting excitation light, an electronic endoscope including an insertion part to be inserted into the body cavity, an imaging device that receives an optical image and outputs image signals corresponding to the optical image, an image forming system that forms the optical image, an operating pant provided at a rear anchor of the insertion part, and a plurality of operable members arranged at the operating part, a display device, an image processing system that receives the image signals outputted from the imaging device, the image processing system obtaining a normal image when the living tissues are illuminated with the white light and a fluorescence image when the living tissues are irradiated with the excitation light, and a control system that controls the whole of the electronic endoscope system. The control system assigns a function to one of the plurality of operable members for switching between a normal mode for observing the normal image and a fluorescence mode for observing the fluorescence image. The control system assigns different functions between the normal mode and fluorescence mode to at least one of the others of the plurality of operable members.

18 Claims, 5 Drawing Sheets

U.S. PATENT DOCUMENTS

| | | |
|---|---|---|
| 2002/0093563 A1* | 7/2002 | Cline et al. .................... 348/65 |
| 2003/0050533 A1* | 3/2003 | Minami ...................... 600/168 |
| 2005/0096505 A1* | 5/2005 | Imaizumi et al. ............ 600/180 |
| 2005/0117028 A1* | 6/2005 | Imaizumi et al. ......... 348/222.1 |
| 2005/0220447 A1 | 10/2005 | Ito |
| 2005/0283047 A1* | 12/2005 | Tashiro et al. ............... 600/118 |
| 2005/0288553 A1 | 12/2005 | Sugimoto |
| 2005/0288556 A1 | 12/2005 | Sugimoto |
| 2006/0020169 A1 | 1/2006 | Sugimoto |

FOREIGN PATENT DOCUMENTS

| | | |
|---|---|---|
| JP | 8-215140 | 8/1996 |
| JP | 2579366 | 11/1996 |
| JP | 2003-180629 | 7/2003 |

OTHER PUBLICATIONS

English Language Abstract of JP 8-215140, (Aug. 1996).

English Language Abstract of JP 2003-180629, (Jul. 2003).

English Language Abstract of Japanese Patent Publication JP 3-009721 Corresponding to JP 2579366, (Jan. 1991).

U.S. Appl. No. 11/275,397 to Sugimoto et al., filed Dec. 29, 2005.

* cited by examiner

| | NORMAL MODE | FLUORESCENCE MODE |
|---|---|---|
| SW1 | TRANSITION TO FLUORESCENCE MODE | TRANSITION TO NORMAL MODE |
| SW2 | FREEZE | ONE STAGE PUSH:FREEZE TWO STAGE PUSH:HARD COPY |
| SW3 | HARD COPY | FLUORESCENCE IMAGE BRIGHTNESS UP |
| SW4 | VIDEO RECORDING START/STOP | FLUORESCENCE IMAGE BRIGHTNESS DOWN |

ELECTRONIC ENDOSCOPE SYSTEM WITH FUNCTIONALLY ALTERABLE OPERABLE MEMBERS

BACKGROUND OF THE INVENTION

The present invention relates to an electronic endoscope system configured to electronically observe and take an image inside a body cavity with an imaging device. In particular, the present invention relates to improvement of function assignment for switches, provided at an operating part of an electronic endoscope of this kind, to be operated by an operator during use.

An electronic endoscope system is provided with an electronic endoscope including an insertion part to be inserted into a body cavity, an operating part to be operated by an operator and, an imaging optical system provided at a distal end of the insertion part, a light source part configured to illuminate the inside of the body cavity with illuminating light being introduced into a light guide provided through the insertion part, and an image processing part configured to process image signals outputted from an imaging device so as to display the processed image signals on a display device such as a monitor.

At the operating part of the electronic endoscope, there is provided a plurality of electrical switches to be operated by an operator during use, in most cases, so that the operator can give instructions to the system, in his own hands during use, on adjustment of an observed image such as light intensity and image density and/or taking a still image.

An electronic endoscope system of this kind, for example, is disclosed in Japanese Unexamined Patent Publication No. P2003-180629. In the system disclosed in Japanese Unexamined Patent Publication No. P2003-180629, when a function for adjusting (increasing and decreasing) a setting value is assigned to any of operation switches A, B, and C provided at an operating part of an electronic endoscope, for a predetermined time period after the adjusting switch for the setting value being turned on, the operation switches B/C are set to carry out not initially assigned functions, but functions as switches for increasing/decreasing the setting value corresponding to the adjusting switch turned on, respectively. In an embodiment described in Japanese Unexamined Patent Publication No. P2003-180629, the operation switches A, B, and C are given functions for freezing an image, adjusting light intensity, and adjusting R density, respectively. When the operation switch B or C is turned on, the operation switches B/C function as switches for increasing/decreasing a corresponding setting value to be adjusted for a predetermined time period.

The system disclosed in Japanese Unexamined Patent Publication No. P2003-180629 is configured to illuminate an inside of a body cavity with white light and take a normal image of the inside of the body cavity illuminated with the white light. In recent years, an electronic endoscope system has been developed, which is capable of taking a fluorescence image of an inside of a body cavity by receiving autofluorescence emitted from a body cavity wall irradiated with an excitation light, as well as taking a normal image. In such an electronic endoscope system, it will be convenient if particular functions for fluorescence image observation are operable at an operating part as well.

However, if the number of push buttons provided at the operating part is increased so as to operate the particular functions for fluorescence image observation in addition to necessary functions for normal image observation, it will be impossible to arrange all the push buttons at convenient positions to operate, and therefore it will be hard to operate some of them.

SUMMARY OF THE INVENTION

The present invention is advantageous in that an electronic endoscope system is provided that is capable of operating particular functions for fluorescence image observation, as well as necessary functions for normal image observation, without increasing the number of push buttons provided at an operating part.

According to an aspect of the present invention, there is provided an electronic endoscope system used for observing living tissues inside a body cavity, which includes an illuminating apparatus having a white light source emitting white light and an excitation light source that emits excitation light having a predetermined wavelength, the living tissues emitting autofluorescence when irradiated with the excitation light, an electronic endoscope, which includes, an insertion part configured to be inserted into the body cavity, a light guide configured to guide the white light and the excitation light to a distal end of the insertion part via the insertion part, an imaging device configured to receive an optical image and output image signals corresponding to the received optical image, an image forming system configured to form the optical image of the living tissues illuminated with each of the white light and the excitation light on the imaging device, an operating part provided at a rear anchor of the insertion part, and a plurality of operable members arranged at the operating part, a display device, an image processing system that receives the image signals outputted from the imaging device, the image processing system obtaining a normal image when the living tissues are illuminated with the white light and a fluorescence image when the living tissues are irradiated with the excitation light, and a control system configured to control the whole of the electronic endoscope system. The control system assigns a function to one of the plurality of operable members for switching between a normal mode for observing the normal image and a fluorescence mode for observing the fluorescence image. The control system assigns different functions between the normal mode and fluorescence mode to at least one of the others of the plurality of operable members.

Optionally, the at least one of the others of the plurality of operable members may include a first operable member to which a first function is assigned in the normal mode, a second operable member to which a second function is assigned in the normal mode, and a third operable member to which a third function is assigned in the normal mode. Optionally, a fourth function for the fluorescence mode may be assigned to one of the first, second, and third operable members. Optionally, a fifth function for the fluorescence mode may be assigned to another one of the first, second, and third operable members. Optionally, at least one of the first, second, and third functions may be assigned to the other of the first, second, and third operable members in the fluorescence mode.

Still optionally, the first function may be a function for giving an instruction of taking a still image. Optionally, the second function may be a function for giving an instruction of printing out an image. Optionally, the third function may be a function for giving an instruction of recording a moving image. Optionally, the fourth function may be a function for giving an instruction of turning up brightness of a fluorescence image. Optionally, the fifth function may be a function for giving an instruction of turning down brightness of a fluorescence image.

Optionally, the image processing system may include a pre-signal-processing element that processes the image signals received from the imaging device, at least two image memories that temporarily store the image signals outputted from the pre-signal-processing element, and a post-signal-processing element that transforms the image signals outputted from the image memories into standardized video signals which are allowed to be displayed on the display device.

Yet optionally, the illuminating apparatus may include a rotary shutter provided in front of the white light source, the rotary shutter having a light transmitting area and a light blocking area, the white light intermittently illuminating the living tissues as the rotary shutter rotates.

Optionally, the illuminating apparatus may include an excitation light source driver that is configured to be able to intermittently turn on/off the excitation light source synchronously with the blocking/transmitting, operation of the rotary shutter.

Further optionally, the image forming system may include an objective lens configured to receive light from the living tissues and forms an image thereof, and an excitation light cut filter provided between the objective lens and the imaging device. Optionally, the excitation light cut filter may eliminate the wavelength components equivalent to the excitation light from light directed to the imaging device from the objective lens.

Preferably, the excitation light source may emit near-ultraviolet light.

DETAILED DESCRIPTION OF THE EMBODIMENTS

Hereinafter, an electronic endoscope system according to an embodiment of the present invention will be described with reference to the accompanying drawings. The electronic endoscope system of the embodiment is directed to a system that is adapted to observe a fluorescence image of autofluorescence emitted from a body cavity wall irradiated with excitation light on a display device such as a monitor, as well as a normal image of the body cavity wall illuminated with white light.

Figure 1:
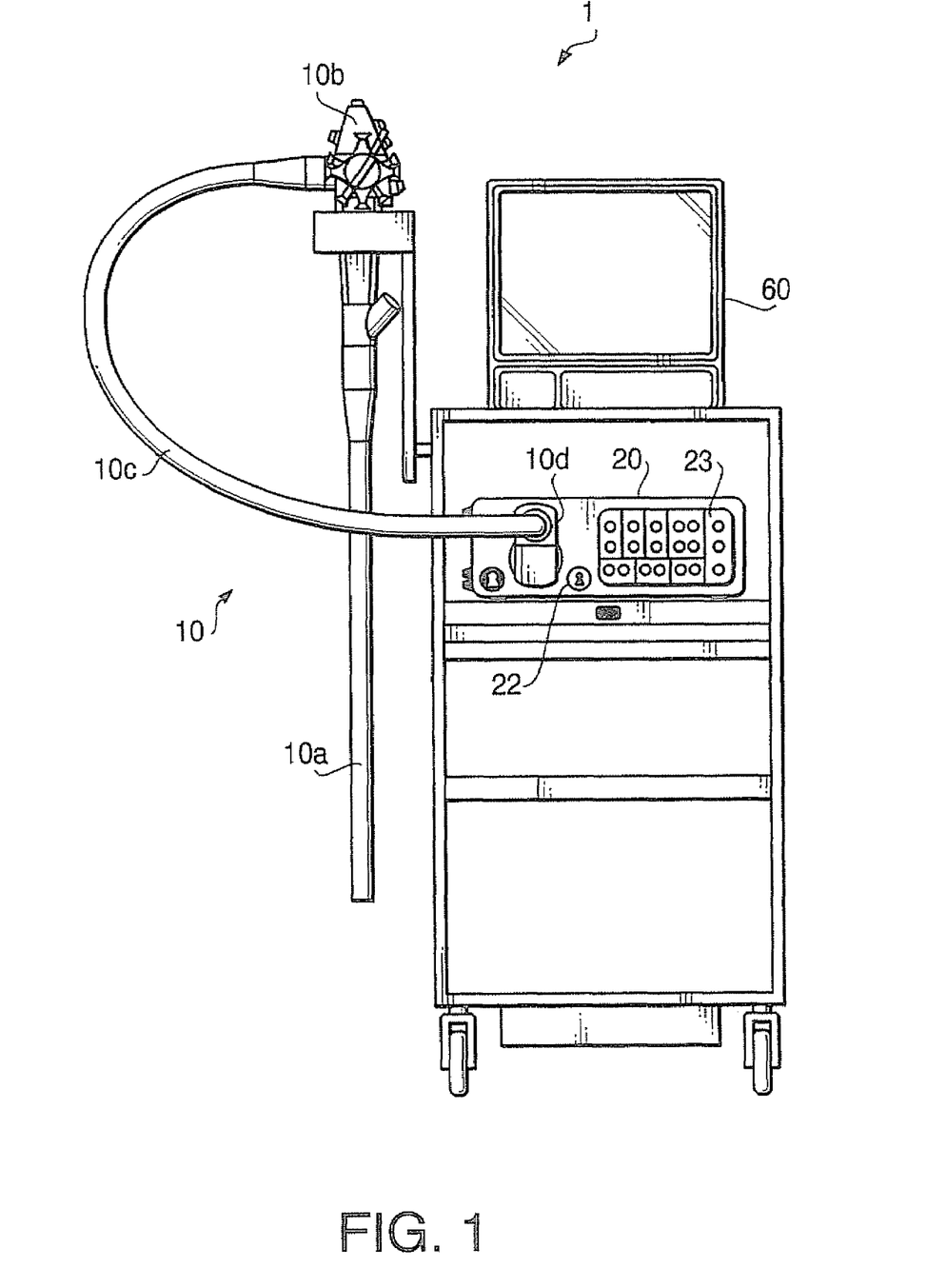
FIG. 1 is a front view of an electronic endoscope system according to an embodiment of the present invention.
Figure 2:
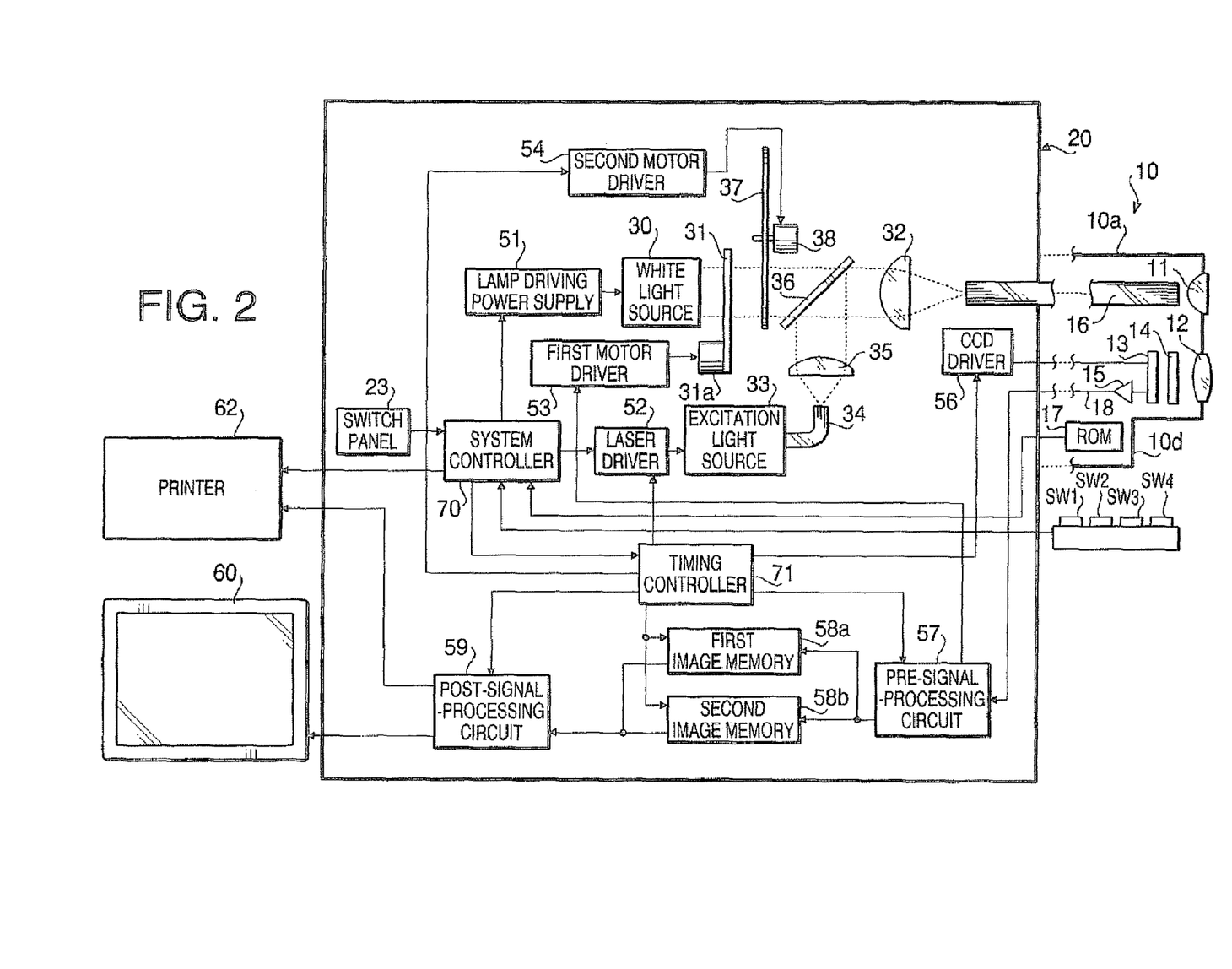
FIG. 2 is a block diagram illustrating an internal configuration of the electronic endoscope system shown in FIG. 1.

FIG. 1 schematically shows an external view of an electronic endoscope system 1 according to an embodiment of the present invention. FIG. 2 shows a block diagram illustrating an internal configuration of the electronic endoscope system 1. As shown in FIG. 1, the electronic endoscope system 1 is provided with a fluorescence observation endoscope 10, a light source apparatus 20, and a monitor 60. In this system, it is possible to select a normal mode for observing a normal image (a colored image obtained by illuminating an object to be observed with white light) or a fluorescence mode for observing a fluorescence image (an image of autofluorescence emitted from living tissues of a body cavity wall irradiated with excitation light).

The fluorescence observation endoscope 10, which is obtained by modifying a usual electronic endoscope so as to be adapted to fluorescence observation, is provided with an insertion part 10a that is formed long and slender so as to be inserted into the body cavity and has a flexible bendable part at the tip thereof, an operating part 10b that includes an angle knob and the like to operate the bendable part of the insertion part 10a, a flexible light guide tube 10c that connects the operating part 10b with a light source apparatus 20, and a connector 10d that is provided at the rear anchor of the flexible light guide tube 10c.

The light source apparatus 20 has a function as a light source part that supplies illuminating light and excitation light to the fluorescence observation endoscope 10, and, as described in detail below, has a function as a video signal generator that generates video signals from image signals taken by the fluorescence observation endoscope 10 and a function as a controlling means that receives signals from a plurality of push button switches provided at the operating part 10b to control the light source part and the video signal generator. On the front surface of the light source apparatus 20, there are provided a key switch 22 for an ON/OFF operation of a main power supply thereof, and a switch panel 23 on which various kinds of operation switches are arranged.

Hereinafter, referring to FIG. 2, particular constitutions of the fluorescence observation endoscope 10 and the light source apparatus 20 will be explained in sequence. On the distal end surface of the insertion part 10a of the fluorescence observation endoscope 10, there are provided a light distribution lens 11 and an objective lens 12. Inside the tip portion of the insertion part 10a, there are incorporated an imaging device 13 such as a CCD color imaging sensor that takes an object's color image formed by the objective lens 12, an excitation light cut filter 14 for eliminating wavelength components equivalent to the excitation light for fluorescence extraction from wavelength components of light directed to the imaging device 13 from the objective lens 12, and a cable driver 15 that amplifies image signals outputted from the imaging device 13.

Figure 3:
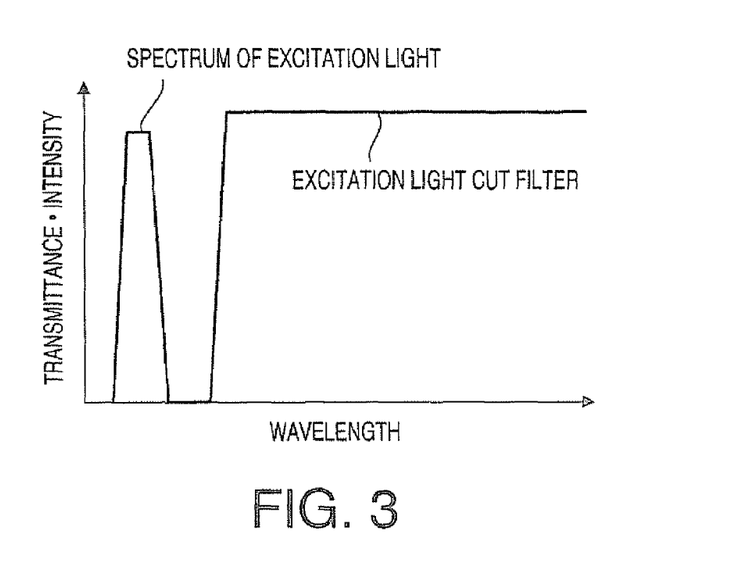
FIG. 3 is a graph illustrating transmission characteristics of an excitation light cut filter provided in an optical system in FIG. 2.

As shown in FIG. 3, the excitation light cut filter 14 has characteristics that cut off the excitation light and transmit light with wavelengths longer than the excitation light. Thereby, it is possible to prevent the excitation light from being incident onto the imaging device 13 and to take only the fluorescence images during fluorescence observation. It is noted that since near-ultraviolet light that excites autofluorescence of a living organism is applied as excitation light, even though the wavelength components of the excitation light is cut off by the excitation light cut filter 14, there is no trouble in talking blue components while taking normal color images.

A signal cable 18 that transmits the image signals amplified by the cable driver 15 runs through the insertion part 10a, the operating part 10b, the flexible light guide tube 10c, and the connector 10d, and is connected to the below-mentioned circuit of the light source apparatus 20 that is connected to the fluorescence observation endoscope 10.

In parallel with the signal cable 18, a light guide 16, which is constituted by bundling a plurality of optical fibers, runs through the insertion part 10a, the operating part 10b, the flexible light guide tube 10c, and the connector 10d. The tip end face of the light guide 16 faces the light distribution lens 11 inside the tip portion of the insertion part 10a, and the rear anchor of the light guide 16 is fixed in the state of being inserted into the light source apparatus 20. In addition, in the connector 10d of the fluorescence observation endoscope 10, there is incorporated a ROM 17 for reading identification data when the connector 10d is attached to the light source apparatus 20.

The light source apparatus 20 selectively introduces either white light for observation of the inside of the body cavity or the excitation light, which excites the living tissues of the body cavity wall such that the living tissues emit autofluorescence, into the end face of the rear anchor of the light guide 16. The light source apparatus 20 further processes the image signals received from the cable driver 15 to generate video signals, and then outputs the video signals to the monitor 60 and the printer 62.

An optical system of the light source apparatus 20 is provided with a white light source (discharge tube lamp) 30 that emits substantially parallel visible light (white light), a light control aperture 31 that controls the beam diameter of the white light emitted from the white light source 30, a condenser lens 32 configured to converge the white light which is transmitted through the light control aperture 31 and to make the white light incident on the end face of the rear anchor of the light guide 16, an excitation light source (laser) 33 that emits the excitation light, an optical waveguide (single fiber) 34 that guides the excitation light emitted from the excitation light source 33, a collimating lens 35 that collimates the excitation light which is diverging light emitted from the optical waveguide 34, and a dichroic mirror 36 that combines both light paths of the white light and the excitation light.

The light control aperture 31 is driven by an aperture driving motor 31a, and functions to control the intensity of the white light. The white light path that extends straight from the white light source 30 to the light guide 16 and the excitation light path that intersects perpendicularly with the white light path are combined by the light path combining device, i.e., the dichroic mirror 36. Since the dichroic mirror 36 transmits the visible light and reflects the near-ultraviolet light with wavelengths shorter than the visible light, the dichroic mirror 36 transmits major part of the white light and reflects the excitation light, introducing both kinds of light into a single light path that extends to the end face of the rear anchor of the light guide 16.

Figure 4:
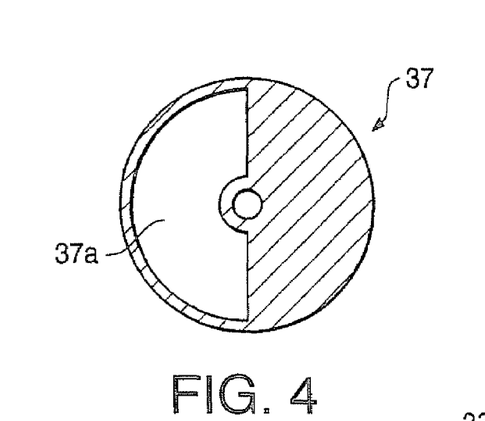
FIG. 4 is a front view of a rotary shutter provided in the optical system in FIG. 2.

Between the white light source 3G and the dichroic mirror 36, there is arranged a rotary shutter 37 that enables the intermittent ON/OFF operation of the white light (that is, intermittently transmits or blocks the white light). The rotary shutter 37, as a front view thereof is shown in FIG. 4, has a fan-shaped window 37a with a center angle of 180 degrees, and the size of the window 37a is configured to be larger than the diameter of the beam of the white light. The rotary shutter 37 is allowed to rotate and intermittently transmit the white light as a shutter driving motor 38 is driven.

The light source apparatus 20 is provided with a lamp driving power supply 51 that supplies a current to the white light source 30, a laser driver 52 that drives and switches the excitation light source 33, a first motor driver 53 that drives the aperture driving motor 31a, a second motor driver 54 that drives the shutter driving motor 38, and a CCD driver 56 that drives the imaging device 13. The light source apparatus 20 further includes a pre-signal-processing circuit 57 that processes image signals received from the cable driver 15, first and second image memories 58a and 58b that temporarily store per field the digital image signals processed and outputted by the pre-signal-processing circuit 57, a post-signal-processing circuit 59 that transforms the digital image signals read out from these image memories into standardized video signals which are allowed to be displayed on the monitor 60 and signals which are allowed to be inputted to the printer 62 and outputs the transformed signals, and a system controller 70 and a timing controller 71 that control the whole of the above components.

When the fluorescence observation endoscope 10 is connected to the light source apparatus 20, the ROM 17 incorporated in the fluorescence observation endoscope 10 is connected to the system controller 70, which identifies that which is connected to the light source apparatus 20 as the fluorescence observation endoscope 10, by reading the identification data stored in the ROM 17.

The system controller 70 is connected with a first, second, third, and fourth push button switches SW1, SW2, SW3, and SW4, which are provided at the operating part 10b of the fluorescence observation endoscope 10. The system controller 70 is also connected with the various kinds of operation switches arranged on the switch panel 23. Based on the setting of each of the switches, the system controller 70 controls the lamp driving power supply 51 and the laser driver 52, so that the white light and the excitation light are consecutively emitted or stopped, and switches a display on the monitor 60.

Figure 5:
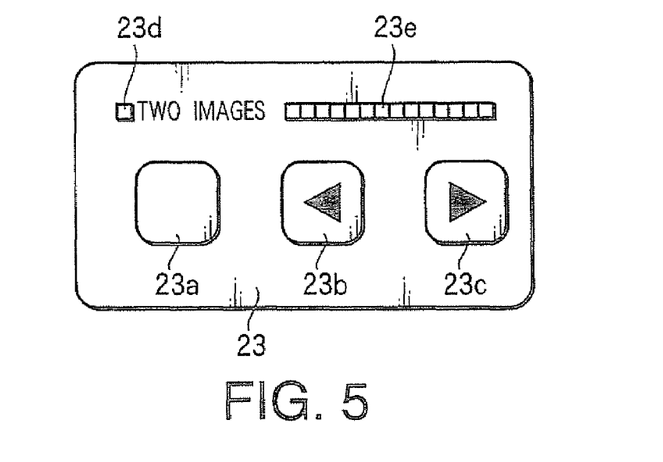
FIG. 5 is a schematic diagram illustrating constitution of a switch panel of the system shown in FIG. 2.

On the switch panel 23, as shown in FIG. 5, there are provided a fluorescence mode display button 23a for selecting either displaying only the fluorescence image or displaying both the fluorescence image and the normal image simultaneously side by side, in the fluorescence mode, and a pair of brightness setting buttons 23b and 23c for up/down, respectively. In addition, the switch panel 23 is provided with a two-image-indicator 23d which lights up when a mode of both the fluorescence image and the normal image being simultaneously displayed side by side is selected in the fluorescence mode and a setting level indicator 23e which visually indicates a target value for the brightness, of each of the fluorescence image and the normal image, set by operating the brightness setting buttons 23b and 23c.

The brightness setting buttons 23b and 23c adjust brightness level of the normal image in the normal mode and brightness level of the fluorescence image in the fluorescence mode. The brightness level of the normal image is adjusted by controlling the aperture driving motor 31a to change the aperture of the light control aperture 30, or by changing the amplification coefficient of the image signals. The brightness level of the fluorescence image is adjusted by changing the light emitting intensity of the excitation light source 33 or by changing the amplification coefficient of the image signals.

The setting level indicator 23e is provided with a two-color light emitting diode, which is capable of emitting green and blue light, at each of level indicating elements. The setting level indicator 23e indicates the brightness level setting with the green light in the normal mode, and indicates the brightness level setting with the blue light in the fluorescence mode.

Figure 6:
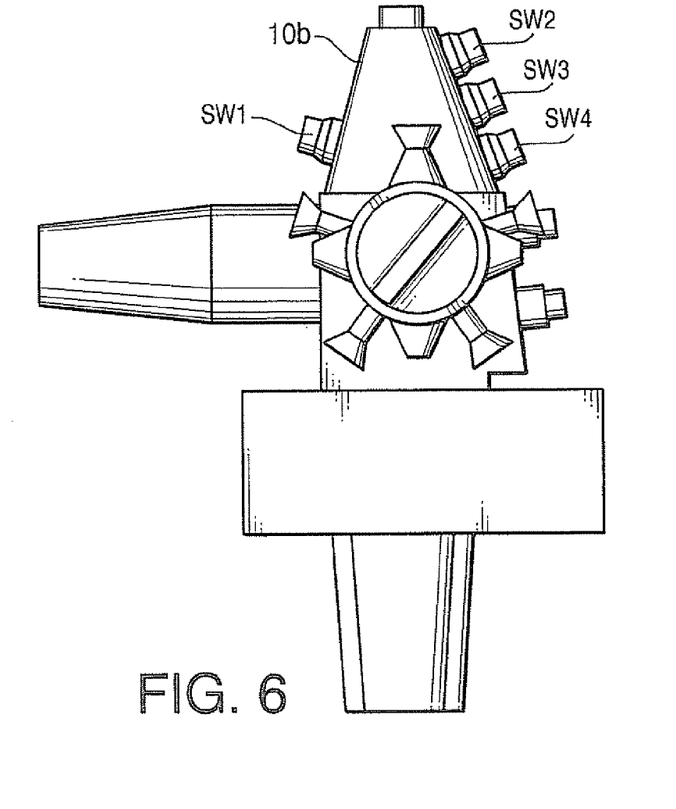
FIG. 6 is an enlarged view of a operating part of the electronic endoscope shown in FIG. 1.

The first, second, third, and fourth push button switches SW1, SW2, SW3, and SW4 are self-returning push button switches. Namely, while an operator is pushing one of the switches, a corresponding function keeps powered on. When the operator stops pushing the switch, the switch returns to the initial state automatically, so that the corresponding function is turned off. These push button switches, as shown in FIG. 6, are provided at the operating part 10b of the fluorescence observation endoscope 10. Only the first push button switch SW1 is located at one side of the operating part 10b, and the second, third, and fourth push button switches SW2, SW3, and SW4 are arranged at the opposite side of the operating part 10b. It is noted that the second push button switch SW2 is a two-stage push button switch.

Based on a command from the system controller 70, the timing controller 71 controls the laser driver 52 to carry out the intermittent ON/OFF operation of the excitation light at predetermined timing, and further controls the second motor driver 54 that drives the shutter driving motor 38 to carry out the intermittent ON/OFF operation of the white light at predetermined timing. The timing controller 71 also controls timing of the imaging device 13 taking an image through the CCD driver 56, and further controls data writing/reading operations of each of the image memories 58a and 58b (i.e., carries out address data control for each of the image memories 58a and 58b), and instructs the pre-signal-processing circuit 57 and the post-signal-processing, circuit 59 on timing to process image signals.

Figure 7:
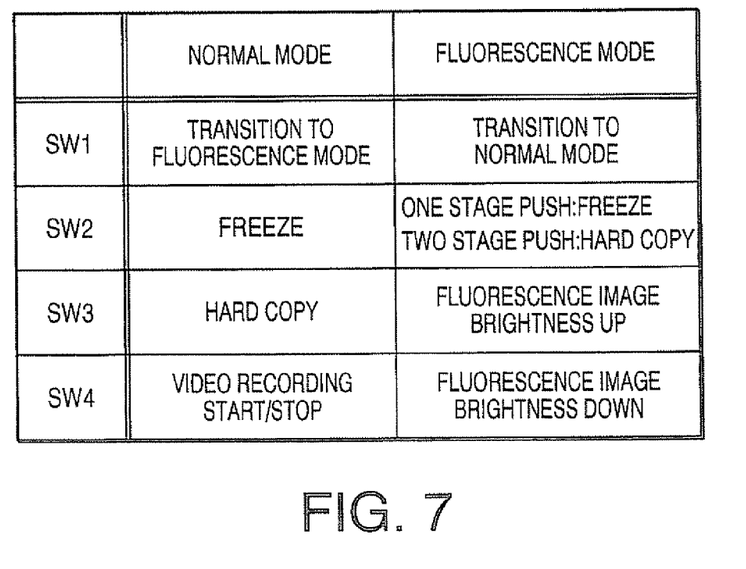
FIG. 7 is a table showing functions assigned to push button switches provided at the operating part.

Next, the assignment of functions to each of the push button switches by the system controller 70 will be explained referring to FIG. 7. When the system controller 70 judges, from the identification data stored in the ROM incorporated in the endoscope, that the endoscope connected with the system controller 70 is an endoscope capable of fluorescence observation, the system controller 70 assigns a function as a mode selector switch, which switches between the normal mode and fluorescence mode, to the first push button switch SW1, and assigns different functions between the normal mode and fluorescence mode to each of the second, third, and fourth push button switches SW2, SW3, and SW4.

In other words, the system controller 70 assigns a function for giving an instruction of "freeze" (talking a still image) to the second push button switch SW2 in the normal mode, while the system controller 70, in the fluorescence mode, assigns to the same switch a function for giving an instruction of "freeze" in the state of the same switch being pushed up to a first stage, and a function for giving an instruction of "hard copy" (printing an image by the printer 62) in the state of the same switch being pushed up to a second stage. In addition, the system controller 70 assigns a function for giving an instruction of "hard copy" to the third push button switch SW3 in the normal mode, and a function for giving an instruction of "fluorescence image brightness up" (turning up brightness of the fluorescence image) in the fluorescence mode. Furthermore, the system controller 70 assigns a function for giving an instruction of "video recording start/stop" (starting/stopping recording an image by a video recorder) to the fourth push button switch SW4 in the normal mode, and a function for giving an instruction of "fluorescence image brightness down" (turning down brightness of the fluorescence image) in the fluorescence mode. It is noted that the functions assigned to the third and fourth push button switches SW3 and SW4 in the fluorescence mode are the same as the functions of the brightness setting buttons 23b and 23c in the fluorescence mode, respectively.

The system controller 70 of the electronic endoscope system in the embodiment assigns the aforementioned functions to the switches arranged at the operating part 10b. As mentioned above, by operating the first push button switch SW1 provided at the operating part 10b of the fluorescence observation endoscope 10, a switching operation between the normal node and fluorescence mode is carried out. When the system is set into the fluorescence mode, there is displayed on the monitor 60 only the fluorescence image (a single display mode) or both of the normal image and fluorescence image side by side (a simultaneous display mode). It is possible to previously select either of these display modes by operating the fluorescence mode display button 23a. Hereinafter, each of the normal mode and fluorescence mode will be described.

In the normal mode, the system controller 70 controls the lamp driving power supply 51 to make the white light source 30 continuously emit white light. The shutter driving motor 38 and the excitation light source 33 remain powered off. The rotary shutter 37 is suspended at such a position that the window 37a of the rotary shutter 37 is on the white light path, and the white light is transmitted through the window 37a. Thereby, the white light emitted from the white light source 30 is continuously introduced into the light guide 16. The imaging device 13 provided at the distal end of the fluorescence observation endoscope 10 takes an image of the inside of the body cavity illuminated with the white light. Normal image signals outputted from the imaging device 13 are inputted to the pre-signal-processing circuit 57 via the signal cable 18.

Figure 8:
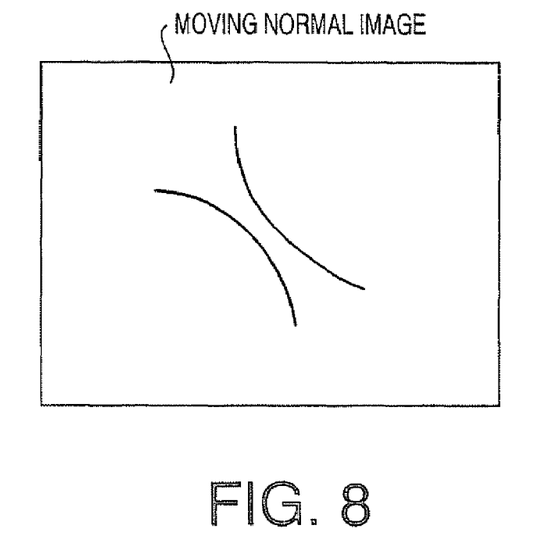
FIG. 8 is an example of a screen displayed on a monitor in a normal mode.

The pre-signal-processing circuit 57 makes the first and second image memories 58a and 58b store the normal image signals based upon a signal issued by the timing controller 71. Based on a signal issued by the timing controller 71, the post-signal-processing circuit 59 reads out the image signals from the first and second image memories 58a and 58b, and converts the image signals into video signals, the video signals being displayed as a moving image on the full-screen of the monitor 60. FIG. 8 shows an example of a screen displayed on the monitor 60 in the normal mode.

In the normal mode, the second push button switch SW2 is pushed up to a first stage, a still normal image is displayed on the monitor 60 according to the instruction of "freeze". This instruction of "freeze" is canceled by pushing the second push button switch SW2 again after stopping pushing the same switch once. The state of the second push button switch SW2 being pushed up to a second stage is not used in the normal mode in addition, when the third push button switch SW3 is set on, a still normal image is printed out from the printer 62 according to the instruction of "hard copy". Further, when the fourth push button switch SW4 is set on once, the system controller 70 controls a video recorder (not shown) to start recording a normal image. When the fourth push button switch SW4 is set on again, the system controller 70 controls the video recorder to stop recording.

When the first push button switch SW1 is set on in the normal mode, the system is set into the fluorescence mode. At this time, the system is also set into a display mode, predetermined by setting of the fluorescence mode display button 23a, between the single display mode, in which a single fluorescence image is displayed on the monitor 60, and the simultaneous display mode in which both of the fluorescence image and normal image are displayed simultaneously on the monitor 60. When the single display mode is selected by the fluorescence mode display button 23a, the system controller 70 controls the lamp driving power supply 51 to turn off the white light source 30, and controls the laser driver 52 to mace the excitation light source 33 emit continuously. At this time, the shutter driving motor 38 remains powered off. Thereby, the excitation light emitted from the excitation light source 33 is reflected by the dichroic mirror 36 to be continuously introduced into the light guide 16. The imaging device 13 provided at the distal end of the fluorescence observation endoscope 10 takes an image of autofluorescence emitted from the body cavity wall excited by the excitation light. Fluorescence image signals outputted from the imaging device 13 are inputted to the pre-signal-processing circuit 57 via the cable driver 15 and the signal cable 18.

The pre-signal-processing circuit 57 makes the first and second image memories 58a and 58b store the fluorescence image signals on the basis of a signal issued from the timing controller 71. The post-signal-processing circuit 59 reads out the image signals from the first and second image memories 58a and 58b, and converts the image signals into video signals, the video signals being displayed as a single moving fluorescence image on the full-screen of the monitor 60.

When the simultaneous display mode is selected by the fluorescence mode display button 23a, the system controller 70 controls the lamp driving power supply 51 to make the white light source 30 continuously emit the white light. The timing controller 71 controls the second motor driver 54 to rotate the shutter driving motor 38, and controls the laser driver 52 to turn off the excitation light source 33 while the window 37a of the rotary shutter 37 is being on the white light path (while the white light is being introduced into the light guide 16), and to turn on the excitation light source 33 while a light blocking area of the rotary shutter 37 is being on the white light path (while the white light is not being introduced into the light guide 16). Thereby, an object is irradiated alternately with the white light and the excitation light. The imaging device 13, provided at the distal end of the fluorescence observation endoscope 10, alternately takes the normal image of the body cavity wall illuminated with the white light and the fluorescence image of autofluorescence emitted from the body cavity wall excited by the excitation light. The image signals outputted from the imaging device 13 are inputted to the pre-signal-processing circuit 57 via the cable driver 15 and the signal cable 18.

Figure 9:
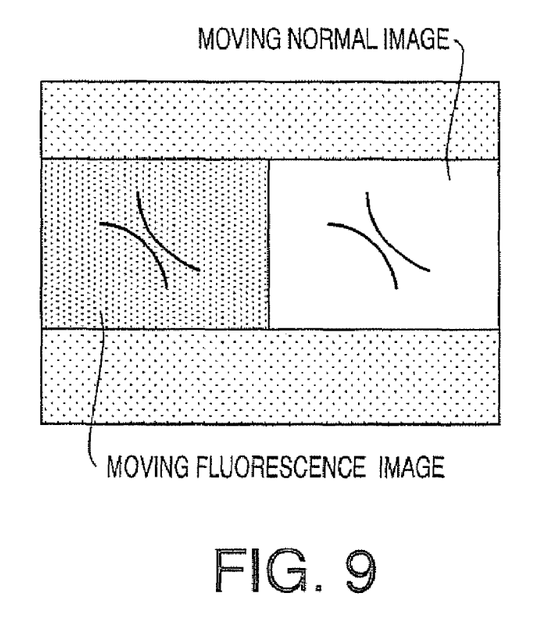
FIG. 9 is an example of a screen displayed on the monitor in a simultaneous display mode in a fluorescence mode.

Based on a signal issued by the timing controller 71, the pre-signal-processing circuit 57 makes the first image memory 58a store the normal image signals, and makes the second image memory 58b store the fluorescence image signals. The post-signal-processing circuit 59 reads out the image signals from each of the first and second image memories 58a and 58b based on a signal issued by the timing controller 71, and scan-converts the read image signals, so that a moving normal image and moving fluorescence image are displayed on the monitor 60. FIG. 9 shows an example of a screen displayed on the monitor 60 in the simultaneous display mode.

In the fluorescence mode including the single display mode and the simultaneous display mode, an operation in the case of each of the push button switches being set on is described as follows. When the first push button switch SW1 is set on, the system is set into the normal mode. When the second push button switch SW2 is pushed up to the first stage once, a still fluorescence image is displayed on the monitor 60 according to the instruction of "freeze". When the second push button switch SW2 is pushed up to the first stage again, the instruction of "freeze" is canceled, so that the moving fluorescence image is displayed on the monitor 60 again. When the second push button switch SW2 is pushed up to the second stage, the still fluorescence image displayed on the monitor 60 is printed out from the printer 62 according to the instruction of "hard copy". When the third push button switch SW3 is set on, the brightness of the fluorescence image is assigned to be turned up. When the fourth push button switch SW4 is set on, the brightness of the fluorescence image is assigned to be turned down.

An operator searches a lesioned part by visually comparing the normal image with the fluorescence image, and compares fluorescence intensities between a normal part and the lesioned part by changing the brightness of the fluorescence image. For these reasons, it will be easy to find and observe the lesioned part, if the brightness of the fluorescence image can be adjusted by the operating part 10b under the operator's hands as described in the aforementioned embodiment.

The present disclosure relates to the subject matter contained in Japanese Patent Application No. P2005-000948, filed on Jan. 5, 2005, which is expressly incorporated herein by reference in its entirely.

What is claimed is:

1. An electronic endoscope system used for observing living tissues inside a body cavity, comprising:
    an illuminating apparatus having a white light source emitting white light and an excitation light source that emits excitation light having a predetermined wavelength, the living tissues emitting autofluorescence when irradiated with the excitation light;
    an electronic endoscope, which includes:
    an insertion part configured to be inserted into the body cavity;
    a light guide configured to guide the white light and the excitation light to a distal end of the insertion part via the insertion part;
    an imaging device configured to receive an optical image and output image signals corresponding to the received optical image;
    an image forming system configured to form the optical image of the living tissues illuminated with each of the white light and the excitation light on the imaging device;
    an operating part provided at a rear anchor of the insertion part; and
    a plurality of operable members arranged at the operating part;
    a display device;
    an image processing system that receives the image signals outputted from the imaging device, the image processing system obtaining a normal image when the living tissues are illuminated with the white light and a fluorescence image when the living tissues are irradiated with the excitation light; and
    a control system configured to control the whole of the electronic endoscope system,
    wherein the control system assigns a function to one of the plurality of operable members for switching between a normal mode for observing the normal image and a fluorescence mode for observing the fluorescence image, and
    wherein the control system assigns different functions between the normal mode and fluorescence mode to at least one of the others of the plurality of operable members.

2. The electronic endoscope system according to claim 1, wherein the at least one of the others of the plurality of operable members includes:
    a first operable member to which a first function is assigned in the normal mode;
    a second operable member to which a second function is assigned in the normal mode; and
    a third operable member to which a third function is assigned in the normal mode,
    wherein a fourth function for the fluorescence mode is assigned to one of the first, second, and third operable members,
    wherein a fifth function for the fluorescence mode is assigned to another one of the first, second, and third operable members, and
    wherein at least one of the first, second, and third functions is assigned to the other of the first, second, and third operable members in the fluorescence mode.

3. The electronic endoscope system according to claim 2,
wherein the first function is a function for giving an instruction of talking a still image,
wherein the second function is a function for giving an instruction of printing out an image,
wherein the third function is a function for giving an instruction of recording a moving image,
wherein the fourth function is a function for giving an instruction of turning up brightness of a fluorescence image, and
wherein the fifth function is a function for giving an instruction of turning down brightness of a fluorescence image.

4. The electronic endoscope system according to claim 3, wherein the image processing system includes:
a pre-signal-processing element that processes the image signals received from the imaging device;
at least two image memories that temporarily store the image signals outputted from the pre-signal-processing element; and
a post-signal-processing element that transforms the image signals outputted from the image memories into standardized video signals which are allowed to be displayed on the display device.

5. The electronic endoscope system according to claim 3, wherein the illuminating apparatus includes a rotary shutter provided in front of the white light source, the rotary shutter having a light transmitting area and a light blocking area, the white light intermittently illuminating the living tissues as the rotary shutter rotates.

6. The electronic endoscope system according to claim 5, wherein the illuminating apparatus includes an excitation light source driver that is configured to be able to intermittently turn on/off the excitation light source synchronously with the blocking/transmitting, operation of the rotary shutter.

7. The electronic endoscope system according to claim 3, wherein the image forming system comprises:
an objective lens configured to receive light from the living tissues and forms an image thereof; and
an excitation light cut filter provided between the objective lens and the imagine device,
wherein the excitation light cut filter eliminates the wavelength components equivalent to the excitation light from light directed to the imaging device from the objective lens.

8. The electronic endoscope system according to claim 7, wherein the excitation light source emits near-ultraviolet light.

9. The electronic endoscope system according to claim 2, wherein the image processing system includes:
a pre-signal-processing element that processes the image signals received from the imaging device;
at least two image memories that temporarily store the image signals outputted from the pre-signal-processing element; and
a post-signal-processing element that transforms the image signals outputted from the image memories into standardized video signals which are allowed to be displayed on the display device.

10. The electronic endoscope system according to claim 2, wherein the illuminating apparatus includes a rotary shutter provided in front of the white light source, the rotary shutter having a light transmitting area and a light blocking area, the white light intermittently illuminating the living tissues as the rotary shutter rotates.

11. The electronic endoscope system according to claim 10, wherein the illuminating apparatus includes an excitation light source driver that is configured to be able to intermittently turn on/off the excitation light source synchronously with the blocking/transmitting operation of the rotary shutter.

12. The electronic endoscope system according to claim 2, wherein the image forming system comprises:
an objective lens configured to receive light from the living tissues and forms an image thereof; and
an excitation light cut filter provided between the objective lens and the imaging device,
wherein the excitation light cut filter eliminates the wavelength components equivalent to the excitation light from light directed to the imaging device from the objective lens.

13. The electronic endoscope system according to claim 12, wherein the excitation light source emits near-ultraviolet light.

14. The electronic endoscope system according to claim 1, wherein the image processing system includes:
a pre-signal-processing element that processes the image signals received from the imaging device;
at least two image memories that temporarily store the image signals outputted from the pre-signal-processing element; and
a post-signal-processing, element that transforms the image signals outputted from the image memories into standardized video signals which are allowed to be displayed on the display device.

15. The electronic endoscope system according to claim 1, wherein the illuminating apparatus includes a rotary shutter provided in front of the white light source, the rotary shutter having a light transmitting area and a light blocking area, the white light intermittently illuminating the living tissues as the rotary shutter rotates.

16. The electronic endoscope system according to claim 15, wherein the illuminating apparatus includes an excitation light source driver that is configured to be able to intermittently turn on/off the excitation light source synchronously with the blocking/transmitting operation of the rotary shutter.

17. The electronic endoscope system according to claim 1, wherein the image forming system comprises:
an objective lens configured to receive light from the living tissues and forms an image thereof; and
an excitation light cut filter provided between the objective lens and the imaging device,
wherein the excitation light cut filter eliminates the wavelength components equivalent to the excitation light from light directed to the imaging device from the objective lens.

18. The electronic endoscope system according to claim 17, wherein the excitation light source emits near-ultraviolet light.

* * * * *